(12) United States Patent
Ikeda et al.

(10) Patent No.: US 6,685,690 B2
(45) Date of Patent: Feb. 3, 2004

(54) DISPOSABLE DIAPER

(75) Inventors: Miyuki Ikeda, Kagawa (JP); Yoshitaka Mishima, Kagawa (JP)

(73) Assignee: Uni-Charm Corporation, Ehime-ken (JP)

( * ) Notice: Subject to any disclaimer, the term of this patent is extended or adjusted under 35 U.S.C. 154(b) by 0 days.

(21) Appl. No.: 10/008,845

(22) Filed: Nov. 13, 2001

(65) Prior Publication Data

US 2002/0115979 A1 Aug. 22, 2002

(30) Foreign Application Priority Data

Nov. 13, 2000 (JP) ........................................ 2000-345696

(51) Int. Cl.⁷ ............................ A61F 13/15; A61F 13/20
(52) U.S. Cl. ................ 604/385.3; 604/369; 604/385.31
(58) Field of Search ..................... 604/369, 385.01, 604/385.31, 383–396, 385.24–385.3

(56) References Cited

U.S. PATENT DOCUMENTS

| | | | |
|---|---|---|---|
| 4,393,865 A | | 7/1983 | Lambert |
| 5,012,540 A | * | 5/1991 | Hockaday ...................... 5/487 |
| 5,196,000 A | * | 3/1993 | Clear et al. ............ 604/385.29 |
| 5,295,986 A | * | 3/1994 | Zehner et al. .......... 604/385.25 |
| 5,643,244 A | * | 7/1997 | Yamaki et al. ......... 604/385.24 |
| 5,649,920 A | * | 7/1997 | Lavon et al. ............ 604/385.3 |
| 5,833,677 A | * | 11/1998 | Sauer .......................... 604/369 |
| 5,868,725 A | * | 2/1999 | Coles et al. ............ 604/385.23 |
| 5,904,675 A | | 5/1999 | Laux et al. |
| 6,315,764 B1 | * | 11/2001 | Faulks et al. ........... 604/385.24 |
| 6,425,889 B1 | * | 7/2002 | Kitaoka et al. ......... 604/685.01 |
| 6,506,185 B1 | * | 1/2003 | Sauer et al. ............ 604/385.01 |

FOREIGN PATENT DOCUMENTS

| | | |
|---|---|---|
| DE | 197 46 500 | 4/1999 |
| EP | 0 091 153 | 10/1983 |
| EP | 0 311 333 | 4/1989 |
| GB | 2 216 774 | 10/1989 |
| JP | A-8-154973 | 6/1996 |
| JP | A-8-317950 | 12/1996 |
| JP | A-8-322876 | 12/1996 |

OTHER PUBLICATIONS definitions of "convex", "concave", "contract" and "compress".*
European search report mailed Mar. 28, 2002.

* cited by examiner

*Primary Examiner*—Karin Reichle
(74) *Attorney, Agent, or Firm*—Butzel Long (57) ABSTRACT

A disposable diaper that has a panel member which is flexible and substantially non-stretchable and attached to an end flap in a rear waist region and extends in a transverse direction of the diaper. The panel member has a stiffness higher than that of the end flap so that shrinkage and/or distortion of the end flap can be restrained by the panel member.

4 Claims, 7 Drawing Sheets

FIG.7

DISPOSABLE DIAPER

BACKGROUND OF THE INVENTION

This invention relates to a disposable diaper that is used to absorb and contain excretion discharged thereon.

Open-type disposable diapers which comprise a liquid-pervious topsheet, a liquid-impervious backsheet and a liquid-absorbent core disposed between these sheets so as to define a front waist region, a rear waist region and a crotch region extending between these waist regions are well known. In such diapers, a pair of end flaps extends outward in the longitudinal direction from longitudinally opposite ends of the core in the front and rear waist regions.

Furthermore, in such diapers an elastic member associated with a waist-opening and being stretchable in a transverse direction is attached under tension to the end flap at least in the rear waist region. Additionally, elastic members associated with leg-openings and being stretchable there along are attached under tension to the respective side flaps. The core comprises a mixture of fluff pulp, high absorbent polymer particles and thermoplastic synthetic resin fibers compressed to a desired thickness. In such an arrangement, the core has stiffness higher than that of the topsheet and backsheet. Such a well known diaper is exemplified in Japanese Patent Application Publication Nos. 1996-154973A, 1996-317950A and 1996-322876A.

In such diapers the end flaps usually have a stiffness that is lower than that in the region of the diaper containing the core. As a result, the contraction of the elastic member associated with the waist-opening may cause a plurality of wrinkles to be formed over substantially entire regions of the end flaps. Alternatively or in addition, movement of the diaper wearer's body may distort the end flaps which are partially formed with wrinkles. The portions of the end flaps which are formed with wrinkles are apt to be spaced apart from the wearer's skin. Thus an undesirable clearance is generated between the wearer's skin and such portions of the end flaps formed with wrinkles through which excretion may leak to the outside of the diaper.

SUMMARY OF THE INVENTION

This invention provides a disposable diaper in which the end flap is well resistant to shrinkage and there is no anxiety that a clearance might be generated between a wearer's skin and the end flap.

According to this invention, there is provided a disposable diaper comprising a liquid-pervious topsheet, a liquid-impervious backsheet and a liquid-absorbent core disposed between these sheets so as to define a front waist region, a rear waist region and a crotch region extending between these waist regions, and a pair of end flaps extending outward in a longitudinal direction of the diaper from longitudinally opposite ends of the core lying in the front and rear waist regions.

The disposable diaper further comprises a panel member which is flexible and substantially non-stretchable and attached to an end flap at least in a rear waist region and extends in a transverse direction and has stiffness that is higher than that of the end flap.

According to one embodiment of this invention, an elastic member associated with the waist-opening and being stretchable in the transverse direction is secured under tension to the end flap at least in the rear waist region, and the panel member lies between the end of the core and the elastic member associated with the waist-opening.

According to another embodiment of this invention, the panel member has transversely opposite side portions and an intermediate portion extending between the transversely opposite side portions and the inner surface of the panel member which faces a wearer's skin curves from the transversely opposite side portions toward the intermediate portion so as to describe circular arcs projecting away from the wearer's skin.

According to still another embodiment of this invention, the intermediate portion of the panel member is shaped to be convex toward the wearer'skin.

According to further another embodiment of this invention, the panel member is made from foamable polyethylene and has a stiffness of about 0.5 mN·cm~150 mN cm as measured by the Gurley Stiffness Test.

DETAILED DESCRIPTION OF THE PREFERRED EMBODIMENTS

Details of a disposable diaper according to this invention will be more fully understood from the description of open-type diaper given hereunder with reference to the accompanying drawings.

Figure 1:
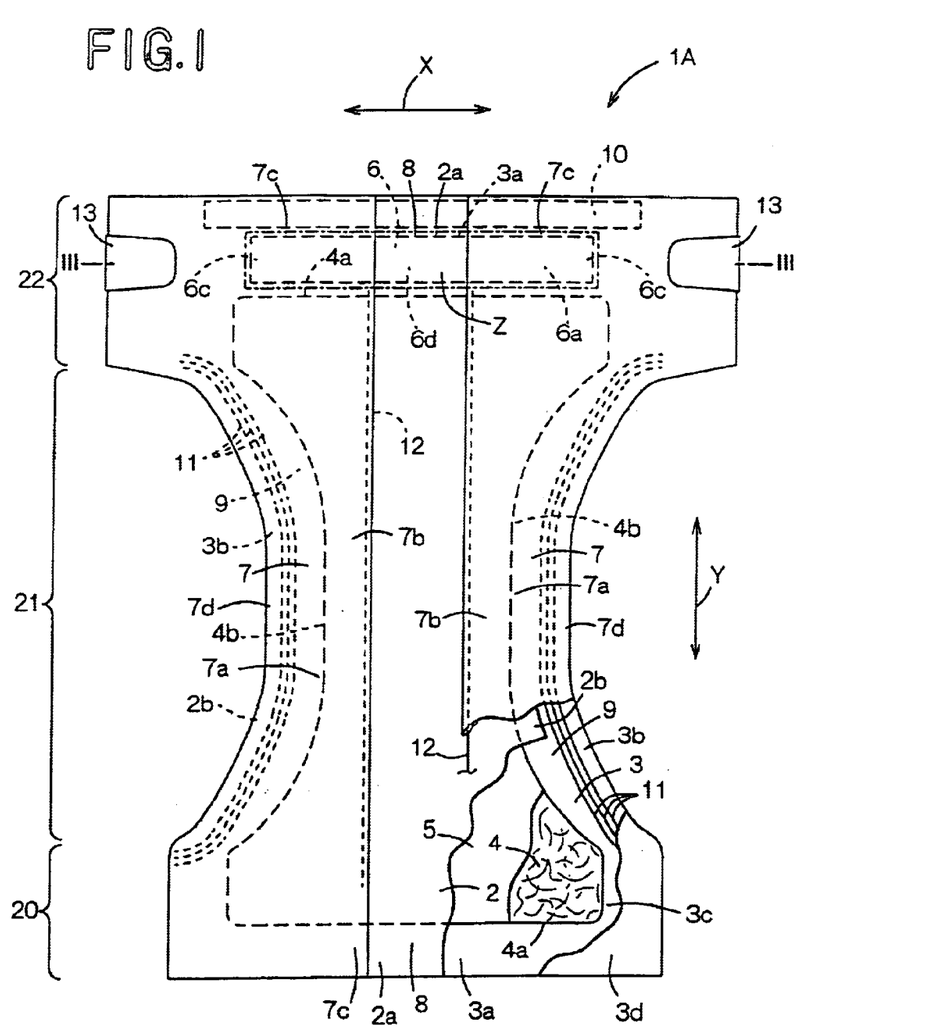
FIG. 1 is a plan view showing a partially cutaway diaper from the side of topsheet.
Figure 2:
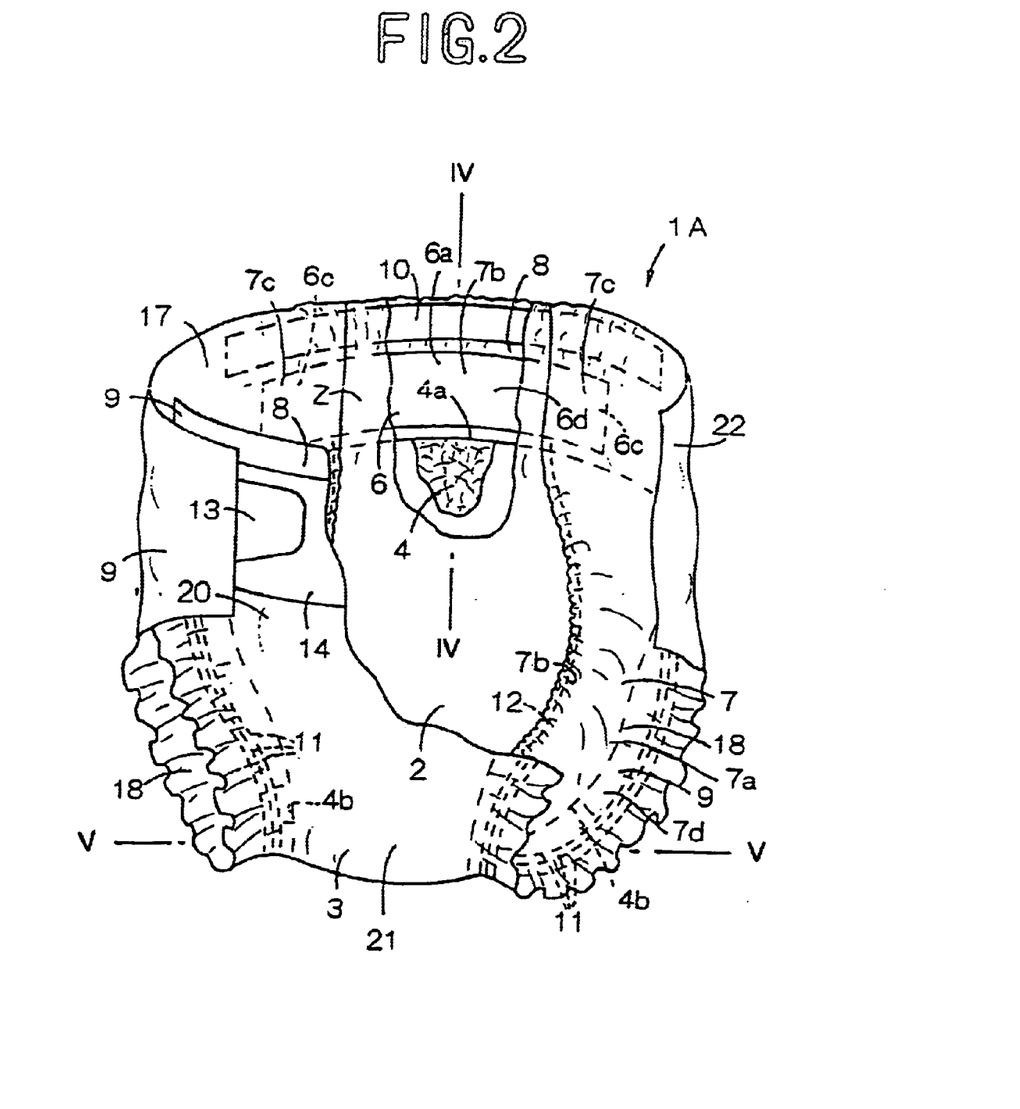
FIG. 2 is a perspective view showing the partially cutaway diaper having its front and rear waist regions connected to each other to be put on a wearer's body.
Figure 3:
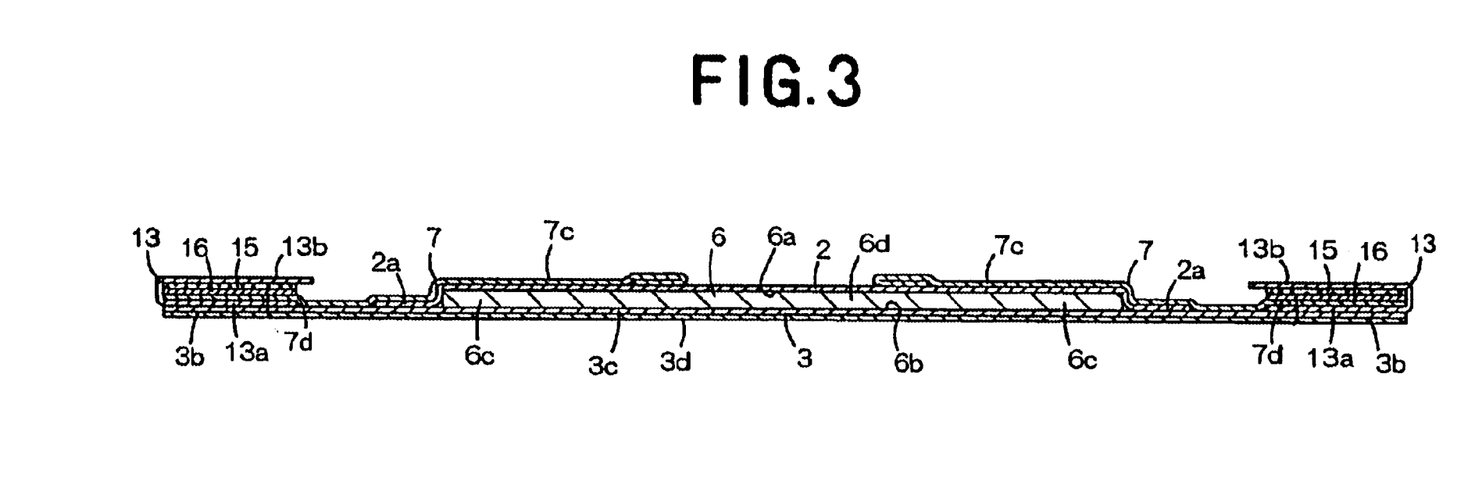
FIG. 3 is a sectional view taken along section line III—III in FIG. 1.

FIG. 1 is a plan view showing an opened and partially cutaway diaper 1A from a topsheet 2, FIG. 2 is a perspective view showing the partially cutaway diaper 1A which is assembled to be put on a wearer's body and FIG. 3 is a sectional view taken along section line III—III in FIG. 1. In FIG. 1, a longitudinal direction is indicated by an arrow Y and a transverse direction is indicated by an arrow X. It is to be understood with respect to description of a panel member 6 given hereinafter that the surface of the panel member 6 with faces the wearer's skin will be referred to as an inner surface 6a and the surface of the panel member 6 which does not face the wearer's skin will be referred to as an outer surface 6b.

The diaper 1A basically comprises a liquid-pervious topsheet 2, a liquid-impervious backsheet 3 which comprises, in turn, a composite sheet composed of a plastic film 3d laminated with a hydrophobic fibrous nonwoven fabric 3c, and a liquid-absorbent core 4 disposed between the topsheet 2 and backsheet, and this entire structure is covered with a diffusion sheet 5 such as tissue paper. The core 4 is joined to the topsheet 2 and backsheet 3 with the diffusion sheet 5 therebetween. The diaper 1A further comprises a panel member 6 which is flexible and substantially non-stretchable and substantially liquid-impervious leak-barrier cuffs 7.

The diaper 1A has a front waist region 20, a rear waist region 22 and a crotch region 21 extending between the front and rear waist regions 20, 22. A pair of end flaps 8 extend outward in the longitudinal direction from longitudinally opposite ends 4a of the core 4 in the front and rear waist regions 20, 22, respectively. A pair of side flaps 9 extend outward in the transverse direction from transversely opposite side edges 4b of the core 4. In the crotch region 21, the side flaps 9 curve inwardly in the transverse direction so as to describe circular arcs. Each of the end flaps 8 is formed from longitudinally opposite end portions 2a, 3a of the topsheet 2 and the backsheet 3. Each of the side flaps 9 is formed from transversely opposite side edge portions 2b, 3b of the topsheet 2 and backsheet 3 and from outermost side portions of the respective leak-barrier cuffs 7.

The end flap 8 of the rear waist region 22 is provided with an elastic member 10 associated with a waist-opening which comprises a plurality of elastic elements that are stretchable in the transverse direction and secured under tension to end flap 8. In the crotch region 21, the side flaps 9 are provided with elastic members 11 associated with leg-openings which comprises a plurality of elastic elements that are stretchable and secured under tension to each of the side flaps 9.

The panel member 6 is shaped in a substantially planar rectangle which is longer in the transverse direction and has inner and outer surfaces 6a, 6b. The panel member 6 lies between the end 4a of the core 4 and the elastic member 10 associated with the waist-opening so as to extend along the end flap 8 adjacent the rear waist region 22 in the transverse direction. The panel member 6 is disposed between the topsheet 2 and backsheet 3 and secured to the topsheet 2 and backsheet 3 in a state free from contractile effect of the elastic members in the longitudinal direction as well as in the transverse direction as best seen in FIG. 1.

The panel member 6 has transversely opposite side portions 6c lying adjacent the respective side flaps 9 and an intermediate portion 6d extending between side portions 6c. The panel member 6 is made from foamable polyethylene and has stiffness higher than that of the end flaps.

The leak-barrier cuffs 7 are provided on the respective side flaps 9 and extend in the longitudinal direction. These leak-barrier cuffs 7 respectively have fixed side edge portions 7a extending in the longitudinal direction in the vicinity of the side edges 4b of the core 4, free side edge portions 7b normally biased in rise above the topsheet 2, and fixed end portions 7c collapsed inwardly of the diaper 1A in the transverse direction.

The leak-barrier cuffs 7 further have outermost side portions 7d extending outwardly beyond the fixed side edge portions 7a in the transverse direction of the diaper 1A. The fixed side edge portions 7a are joined to the side edge portion 2b of the topsheet 2 forming the respective side flaps 9. The fixed end portions 7c are joined to the end portion 2a of the topsheet 2 forming the respective end flaps 8. Elastic members 12 which are stretchable in the longitudinal direction are bonded under tension to the free side edge portions 7b and covered with portions of the respective free side edge portions 7b.

The side flap 9 of the rear waist region 22 is provided with a pair of tape fasteners 13 that extend inward in the transverse direction. The tape fasteners 13 respectively have proximal end portions 13a disposed between the side edge portions 3b of the backsheet 3 and the outermost side portions of the respective leak-barrier cuffs 7 and joined to backsheet 3 and leak-barrier cuffs 7. Free end portions 13b of the respective tape fasteners 13 are coated with pressure-sensitive adhesive 15. These free end portions 13b of the tape fasteners 13 are releasably fixed to release film strips 16 which are made of plastic material and joined to the outermost side edge portions 7d of the respective leak-barrier cuffs 7, by means of pressure-sensitive adhesive 15. The front waist region 20 is provided with a rectangular target tape strip 14 made of a plastic film. This target tape strip 14 serves as a landing zone for the tape fasteners 13.

To wear the diaper 1A, the side flaps 9 in the rear waist region 22 are placed upon outer sides of the respective side flaps 9 in the front waist region 20 and the free end portions 13b of the tape fasteners 13 are anchored to the target tape strip 14 by means of pressure-sensitive adhesive 15 to connect the front waist region 20 with the rear waist region 22. The panel member 6 is flexible and curves to adapt a waist line of the wearer as the diaper 1A is worn.

With the front and rear waist regions 20, 22 connected to each other, the diaper 1A defines a waist-opening 17 and a pair of leg-opening 18 as seen in FIG. 2. The diaper 1A curves in the longitudinal direction with the topsheet 2 inside and the free side edge portions 7b of the respective leak-barrier cuffs 7 rise above the topsheet 2 as the elastic members 12 contract.

In the diaper 1A according to this invention, the panel member 6 has a stiffness higher than that of the end flap 8 and is attached to the end flap 8 so that the movement of the end flap 8 is restrained by the panel member 6. Even if contraction of the elastic member 10 associated with the waist-opening tends to contract the end flap 8 and/or the movement of the wearer of the diaper 1A tends to distort the end flap 8, such effects on the end flap 8 are restrained by the panel member 6. Accordingly, the diaper 1A of the present invention alleviates are eliminates a possibility that the end flap 8 might contract and a clearance might be generated between a region Z of the end flap 8 in which the panel member 6 is attached thereto (as indicated by an imaginary line in FIG. 6) and the wearer's skin.

The panel member 6 preferably has a stiffness of about 0.5 mN·cm~150 mN·cm as measured by the Gurley Stiffness Test. With the stiffness of the panel member 6 lower than about 0.5 mN·cm, it would be impossible for the panel member 6 to prevent the possibility of shrinkage and/or distortion from occurring in the end flap 8. With the stiffness of the panel member 6 exceeding about 150 mN·cm, the region Z of the end flap 8 would have an excessively high stiffness which would create a feeling of discomfort for the wearer of the diaper 1A.

The end flaps 8 and the side flaps 9 preferably have a stiffness of about 0.2 mN·cm~1.0 mN·cm to maintain a desired flexibility of these flaps 8,9. Such values of stiffness were measured according to JIS (Japanese Industrial Standards) L 1096 (6.20.1).

Figure 4:
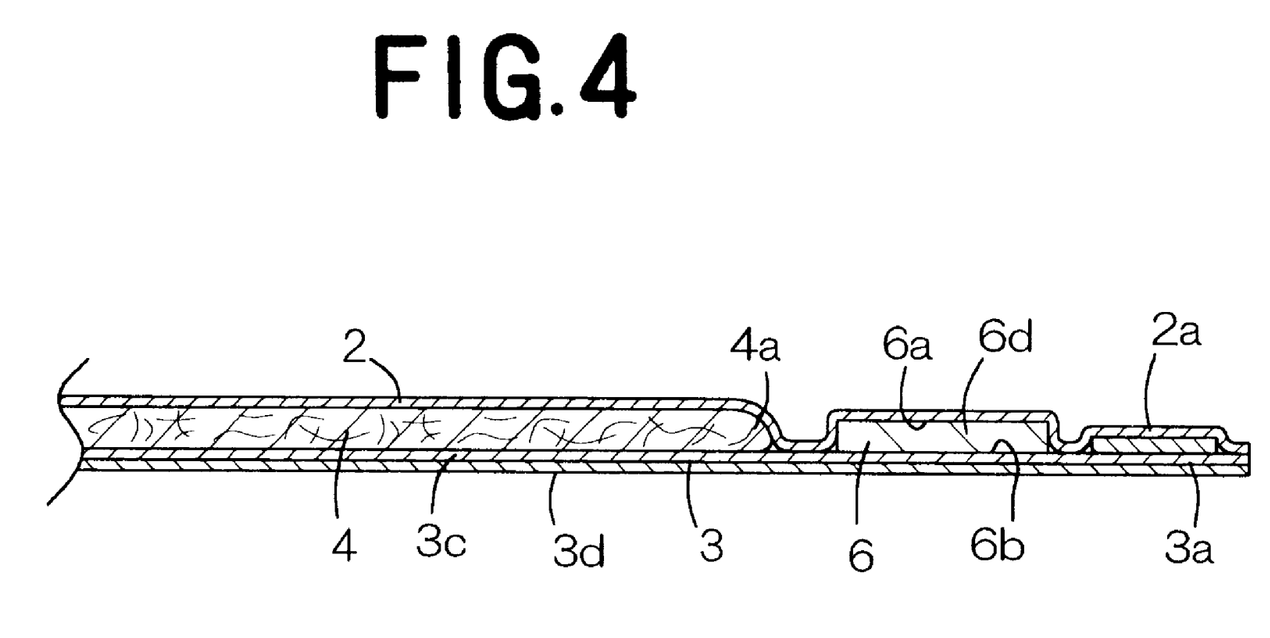
FIG. 4 is a sectional view taken along section line IV—IV in FIG. 2.
Figure 5:
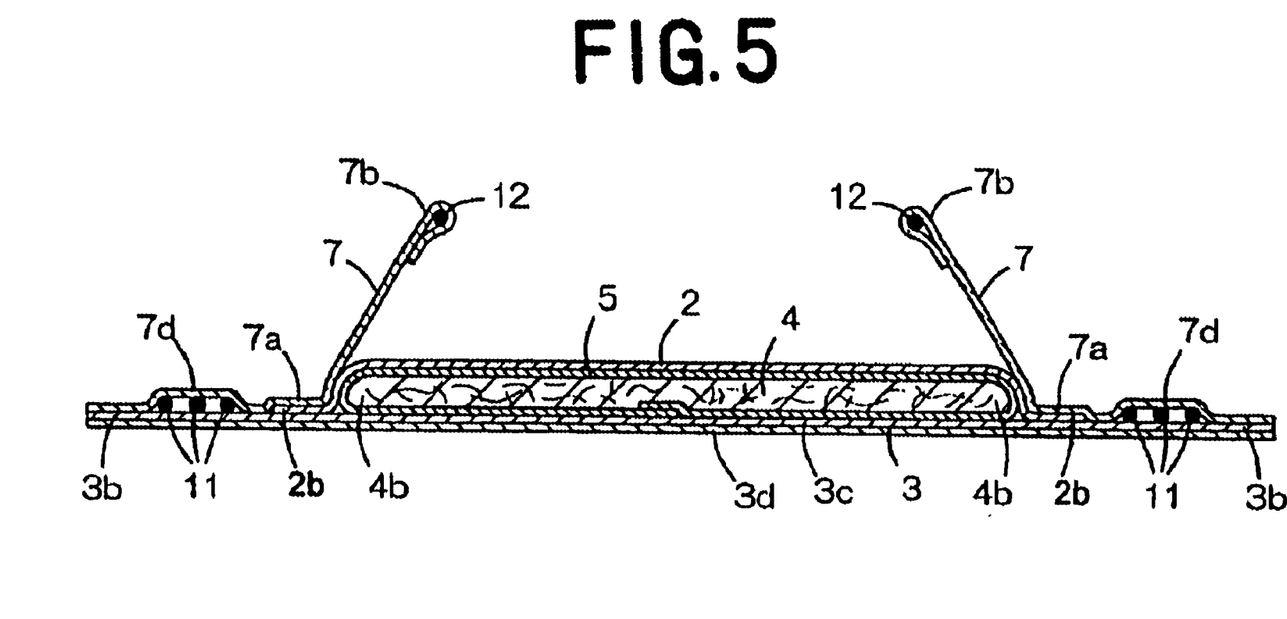
FIG. 5 is a sectional view taken along section line V—V in FIG. 2.

FIG. 4 is a sectional view taken along section line IV—IV in FIG. 2 and FIG. 5 is a sectional view taken along section line V—V in FIG. 2. As seen in FIG. 4, the end flap 8 is formed from end portions 2a, 3a of the topsheet 2 and backsheet 3 that extend outward beyond the longitudinal end 4a of the core 4 in the longitudinal direction and are placed upon and joined to each other. The elastic member 10 associated with the waist-opening is disposed between and joined to end portions 2a, 3a of the topsheet 2 and backsheet 3.

In the side flaps 9, the side edge portions 2b of the topsheet 2 extend slightly outward beyond the side edges 4b of the core 4 in the transverse direction. The side edge portions 3b of the backsheet 3 as well as the outermost side edge portions 7d of the leak-barrier cuffs 7 extend outward beyond the side edge portions 2b of the topsheet 2. The side edge portions 2b are disposed between the side edge portions 3b and the outermost side edge portions 7d and bonded to side edge portions 3b and outermost side edge portions 7d. The side edge portions 3b and the outermost side edge portions 7d are placed upon and bonded one to another. The elastic members 11 associated with the leg-openings are disposed between the side edge portions 3b and the outermost side edge portions 7d of the respective leak-barrier cuffs 7 and bonded to side edge portions 3b and outermost side edges portions 7d.

Figure 6:
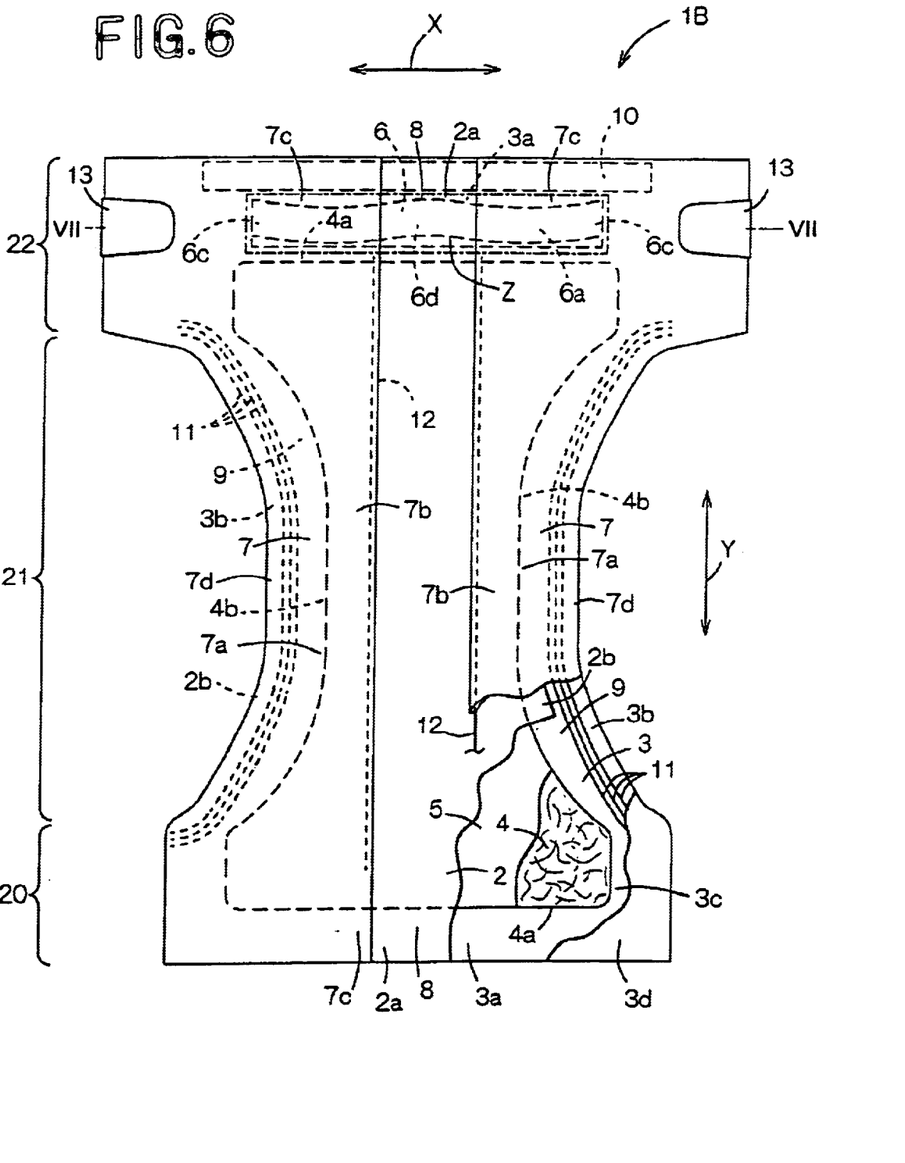
FIG. 6 is a view similar to FIG. 1 showing the partially cutaway diaper according to an alternative embodiment of this invention.
Figure 7:
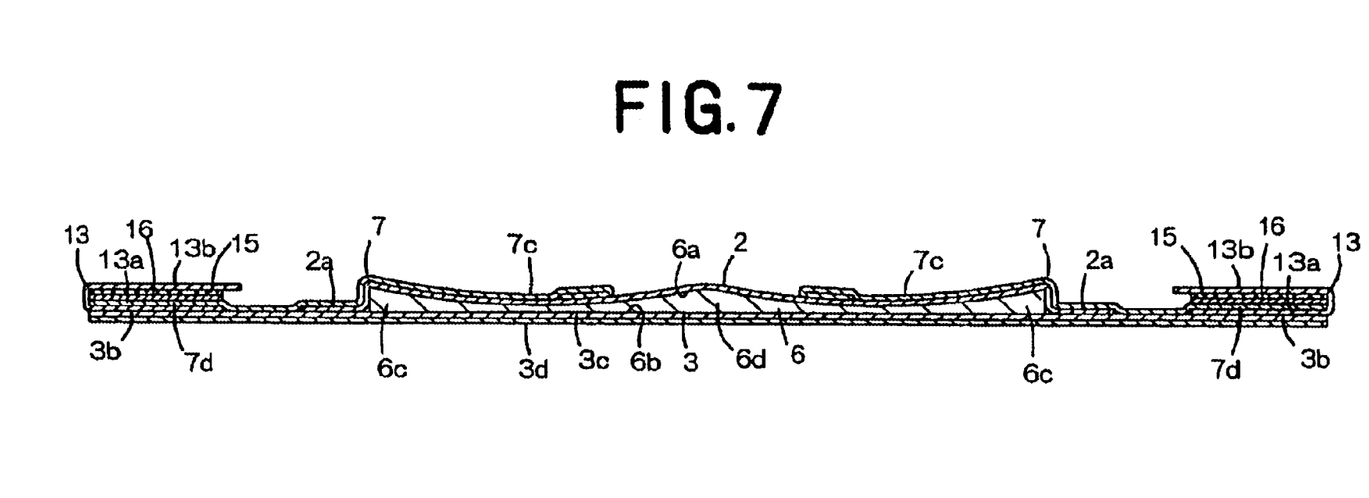
FIG. 7 is a sectional view taken along section line VII—VII in FIG. 6.

FIG. 6 is a view similar to FIG. 1 but showing a disposable diaper 1B according to an alternative embodiment of this invention and FIG. 7 is sectional view taken along section line VII—VII in FIG. 6. The diaper 1B shown in FIG. 6 is structurally distinguishable from the diaper 1A shown in FIG. 1 as follows. The inner surface 6a of the panel member 6 curves away from the wearer's skin so as to describe circular arcs between transversely opposite end portions 6c of panel member 6 and the intermediate portion 6d of panel member 6 is curved so as to be convex toward the wearer's skin.

When the diaper 1D is worn, the transversely opposite end portions 6c of the panel member 6 follow bulges on the wearer's back in the vicinity of the ilia and the intermediate portion 6d of the panel member follows a depression on the wearer's back in the vicinity of the lumbar. Consequently, the inner surface 6a of the panel member 6 comes in close contact with the wearer's skin.

With this diaper 1B the panel member 6 prevents the end flap 8 from shrinking due to contraction of the elastic member 10 associated with the waist-opening and/or prevents the end flap 8 from being distorted due to the wearer' movement. In this way, the possibility that the end flap 8 might shrink is alleviated and the anxiety that a clearance might be generated between the region Z of the end flap 8 and the wearer's skin is eliminated.

The topsheet 2 may be made of a hydrophilic fibrous nonwoven fabric or a porous plastic film. The backsheet 3 may be made of a hydrophobic fibrous nonwoven fabric or a liquid-impervious plastic film. The leak-barrier cuffs 7 may be made of a hydrophobic fibrous nonwoven fabric.

It is also possible to make the backsheet 3 and the leak-barrier cuffs 7 from a composite nonwoven fabric consisting of a melt blown fibrous nonwoven fabric having high water-resistance and two layers of a spun bond fibrous nonwoven fabric having high strength and flexibility.

The nonwoven fabric may be selected from a group including spun lace-nonwoven fabric, needle punch-nonwoven fabrics, melt blown-nonwoven fabrics nonwoven fabrics, thermal bond-nonwoven fabrics, spun bond-nonwoven fabrics, chemical bond-nonwoven fabrics and air through-nonwoven fabrics. The component fibers of the nonwoven fabric may be selected from a group including polyolefine, polyester, and polyamide fibers, and polyethylene/polypropylene and polyethylene/polyester core-sheath-type or side-by-side type conjugated fibers.

The core 4 is formed of a mixture of fluff pulp, high absorption polymer particles and thermoplastic synthetic resin fibers compressed to a desired thickness. The high absorption polymer may be selected from a group including starch-based and cellulose-based polymer and synthetic polymer.

It is also possible according to one embodiment of the present invention to attach the panel member 6 to the end flap 8 in the front waist region 20. The panel member 6 may be made not only from a foamable polyethylene sheet but also from a flexible and substantially non-stretchable plastic sheet or a mat-like sheet consisting of a plurality of non-stretchable fibrous nonwoven fabric layers. The panel member 6 is not limited to having a rectangular shape. The panel member 6 may have other optional shapes such as transversely elongated elliptical or trapezoidal shapes.

Joining of the topsheet 2 and backsheet 3 to each other, fixing of the panel member 6 and the leak-barrier cuffs 7, joining of the core 4 and attachment of the elastic members 10, 11, 12 may be carried out using hot melt adhesive or a heat welding technique such as heat-sealing or sonic sealing.

In addition to the open-type diaper 1A, 1B, the present invention is applicable to pants-type diapers in which the front and rear waist regions are connected to each other.

The disposable diaper according to this invention comprises a panel member attached to the end flap at least in the rear waist region and extending in the transverse direction. This panel member serves to restrain or eliminate anxiety that the end flap might shrink due to contraction of the elastic member associated with the waist-opening and the end flap might be distorted due to the wearer's movement. In this way, the possibility that the end flap might shrink can be alleviated and the apprehension that a clearance might be generated between the region of the end flap in which the panel member is attached to the end flap and the wearer's skin is eliminated.

In the embodiment wherein the inner surface of the panel member curves away from the wearer's skin so as to describe circular arcs between its transversely opposite end portions and in which the intermediate portion is curved so as to be convex toward the wearer's skin, shrinkage and distortion of the end flap are prevented by the panel member and in addition, the fit of the panel member against the wearer's skin is improved in comparison with the case in which the inner surface of the panel member is substantially flat. This is because the inner surface of the curved panel member follows the contour of the waist line along the wearer's back.

What is claimed is:

1. A disposable diaper comprising:
   a liquid-pervious topsheet;
   a liquid-impervious backsheet;
   a liquid-absorbent core disposed between the liquid-pervious topsheet and the liquid-impervious backsheet;
   a front waist region;
   a rear waist region;
   a crotch region extending between the front waist region and the rear waist region;
   said topsheet and said backsheet extending outward in a longitudinal direction of said diaper from longitudinally opposite ends of said liquid-absorbent core which ends lie in said front and rear waist regions, respectively, to define a pair of end flaps; and
   a panel member which is flexible, substantially non-stretchable, and non-contractible, and positioned between the topsheet and backsheet of the end flap at least in the rear waist region so as to extend in a transverse direction of said diaper, said panel member having transversely opposite side portions and an intermediate portion extending between said transversely opposite side portions and wherein an inner surface of said panel member adapted to face a wearer's skin in use curves from said transversely opposite side portions toward said intermediate portion so as to describe circular arcs that are concave toward the wearer's skin in use and that intersect at said intermediate portion of the panel member whereby the inneer surface of the panel member at the intermediate portion of the panel member is convex toward the wearer's skin in use, and said panel member having a stiffness that is higher than a stiffness of the end flap in at least the rear waist region so as to prevent portions of at least the rear waist region from developing a clearance with respect to a waist of a wearer of the diaper.

2. The disposable diaper according to claim 1, wherein said panel member comprises a foamable polyethylene and has a stiffness of about 0.5 mN·cm to about 150 mN·cm.

3. A disposable diaper comprising:
   a liquid-pervious topsheet;
   a liquid-impervious backsheet;
   a liquid-absorbent core disposed between the liquid-pervious topsheet and the liquid-impervious backsheet;
   a front waist region;
   a rear waist region;
   a crotch region extending between the front waist region and the rear waist region;
   said topsheet and said backsheet extending outward in a longitudinal direction of said diaper from longitudinally opposite ends of said liquid-absorbent core which ends lie in said front and rear waist regions, respectively, to define a pair of end flaps; and
   a panel member which is flexible, substantially non-stretchable, and non-contractible, and positioned between the topsheet and backsheet of the end flap at least in the rear waist region so as to extend in a transverse direction of said diaper, said panel member having transversely opposite side portions and an intermediate portion extending between said transversely opposite side portions and wherein an inner surface of said panel member adapted to face a wearer's skin in use curves from said transversely opposite side portions toward said intermediate portion so as to describe circular arcs that are concave toward the wearer's skin in use and that intersect at said intermediate portion of the panel member whereby the inner surface of the panel member at the intermediate portion of the panel member is convex toward the wearer's skin in use, and said panel member having a stiffness that is higher than a stiffness of the end flap in at least the rear waist region;
   a waist-opening; and
   an elastic member provided adjacent the waist-opening, the elastic member being stretchable in said transverse direction and secured under tension to said end flap at least in said rear waist region and said panel member being positioned between the end of said liquid-absorbent
   core in at least the rear waist region and said elastic member in a state free from contractile effect of the elastic member in the longitudinal direction as well as in the transverse direction.

4. The disposable diaper according to claim 3, wherein said panel member comprises a foamable polyethylene and has a stiffness of about 0.5 mN·cm to about 150 mN·cm.

* * * * *